(12) United States Patent
Mou et al.

(10) Patent No.: US 11,255,323 B2
(45) Date of Patent: Feb. 22, 2022

(54) DRIVING SYSTEM FOR ACTUATING AND SENSING MODULE

(71) Applicant: Microjet Technology Co., Ltd., Hsinchu (TW)

(72) Inventors: Hao-Jan Mou, Hsinchu (TW); Chi-Feng Huang, Hsinchu (TW); Yung-Lung Han, Hsinchu (TW); Chang-Yen Tsai, Hsinchu (TW); Wei-Ming Lee, Hsinchu (TW); Hsuan-Kai Chen, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 790 days.

(21) Appl. No.: 16/014,939

(22) Filed: Jun. 21, 2018

(65) Prior Publication Data

US 2019/0033177 A1 Jan. 31, 2019

(30) Foreign Application Priority Data

Jul. 27, 2017 (TW) .................. 106125324

(51) Int. Cl.
*G01N 33/00* (2006.01)
*G01N 1/22* (2006.01)
*F04B 43/04* (2006.01)
*F04D 33/00* (2006.01)

(52) U.S. Cl.
CPC ............ *F04B 43/046* (2013.01); *F04D 33/00* (2013.01); *G01N 1/2273* (2013.01); *G01N 33/0011* (2013.01)

(58) Field of Classification Search
CPC ... F04B 43/046; F04D 33/00; G01N 33/0011; G01N 1/2273
See application file for complete search history.

(56) References Cited

U.S. PATENT DOCUMENTS

| 2004/0037718 | A1 | 2/2004 | Xie et al. | |
| 2014/0377099 | A1* | 12/2014 | Hsueh | F04B 49/22 417/413.2 |
| 2015/0219608 | A1* | 8/2015 | Choi | G06F 3/017 73/23.2 |
| 2016/0353186 | A1* | 12/2016 | Rothkopf | H04R 1/028 |
| 2017/0047764 | A1* | 2/2017 | Lee | H02J 7/0021 |

FOREIGN PATENT DOCUMENTS

| CN | 103576336 A | 2/2014 |
| CN | 103940468 A | 7/2014 |
| CN | 104198346 A | 12/2014 |
| CN | 105874520 A | 8/2016 |
| CN | 205538890 U | 8/2016 |
| CN | 205749040 U | 11/2016 |
| CN | 206038594 U | 3/2017 |
| CN | 206129568 U | 4/2017 |
| JP | 3812917 B2 | 8/2006 |
| TW | M541542 U | 5/2017 |
| TW | M543870 U | 6/2017 |

* cited by examiner

*Primary Examiner* — Dennis White
(74) *Attorney, Agent, or Firm* — Birch, Stewart, Kolasch & Birch, LLP

(57) ABSTRACT

A driving system for an actuating and sensing module includes an actuating and sensing device and a power supply device. The actuating and sensing device includes a sensor, an actuating device, a microprocessor, and a power controller. The power supply device transfers an energy to the power controller, thereby enabling the sensor and the actuating device.

21 Claims, 9 Drawing Sheets

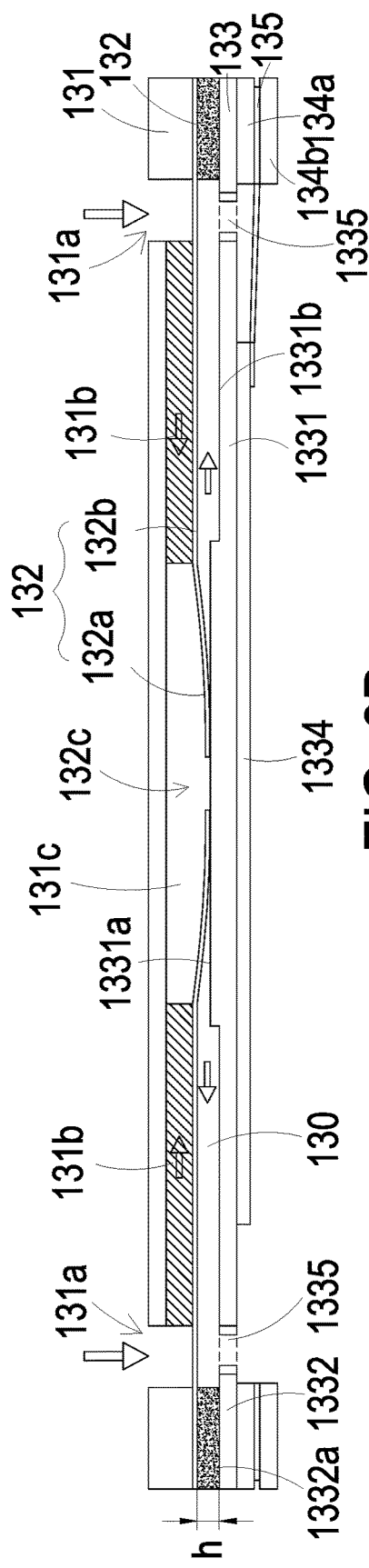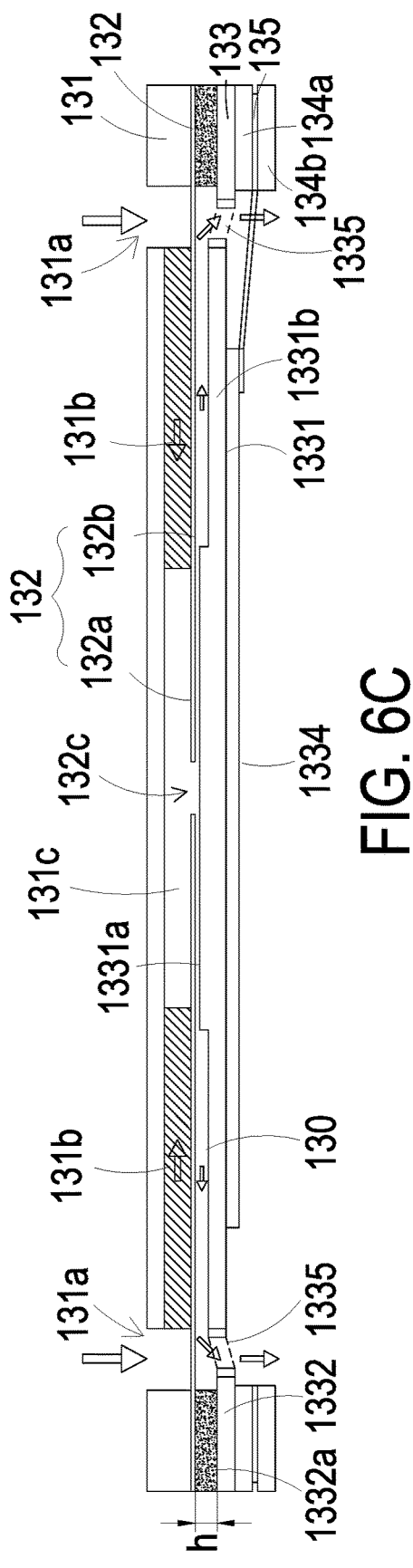

DRIVING SYSTEM FOR ACTUATING AND SENSING MODULE

FIELD OF THE INVENTION

The present disclosure relates to an environmental monitoring system for an actuating and sensing module, and more particularly to a driving system for an actuating and sensing module.

BACKGROUND OF THE INVENTION

Nowadays, people pay much attention to the devices and methods of monitoring the air quality in the environment. For example, it is important to monitor carbon monoxide, carbon dioxide, volatile organic compounds (VOC), PM2.5, and so on. The exposure of these gases in the environment will cause human health problems or even harm the life. Therefore, it is important for every country to develop and implement the environmental monitoring technology.

Generally, it is feasible to use an ambient sensor to monitor the air quality in the environment. If the ambient sensor is capable of immediately providing people with the monitored information relating to the environment for caution, it may help people escape or prevent from injuries and influence on human health caused by the gas exposure in the environment. In other words, the ambient sensor is suitably used for monitoring the ambient air in the environment.

Generally, the ambient sensor is used to monitor the environment and provide information about the environment to the user. As known, the monitoring sensitivity and the precision of the ambient sensor should be taken into consideration. If the airflow is transferred to the ambient sensor through natural convection, the amount of the airflow to be received by the ambient sensor is neither stable nor uniform. Under this circumstance, the result of monitoring the environment is usually not accurate. Moreover, since the airflow is transferred to the ambient sensor through natural convection, the response time of the ambient sensor to monitor the ambient sensor is much longer. In other words, the real-time monitoring efficacy is low.

Nowadays, a large-scale environmental monitoring base station is provided to monitor the ambient air quality. However, the large-scale environmental monitoring base station is only suitable for monitoring the ambient air quality in a large area. If the large-scale environmental monitoring base station is used to monitor the air quality in a small area where human activities exist (e.g., the indoor air quality and the ambient air surrounding us), the monitoring result is usually not accurate and can't be acquired quickly. If the sensor is integrated into a portable electronic device, the air quality can be immediately monitored everywhere and at any time. Moreover, the monitored data can be transmitted to a cloud database in real time so as to be constructed and managed. Consequently, the monitored data of the air quality can be accurately and immediately provided. Under this circumstance, an air quality notification mechanism and an air quality processing mechanism are enabled.

Therefore, there is a need of providing a driving system for an actuating and sensing module for increasing the monitoring accuracy of the sensor, increasing the monitoring speed of the sensor, immediately monitoring the air quality everywhere and at any time, transmitting the monitored data to the cloud database to construct and manage the monitored data, and enabling the air quality notification mechanism and the air quality processing mechanism.

SUMMARY OF THE INVENTION

An object of the present disclosure provides a driving system for an actuating and sensing module. The system includes an actuating and sensing device and a power supply device. The actuating and sensing device includes at least one sensor, at least one actuating device, a microprocessor and a power controller, which are integrated as a modularized structure. The actuating device is used to increase the flow rate of fluid and provide the amount of fluid stably and uniformly. Since the sensor is provided with the amount of the fluid stably and uniformly, the response time of the sensor to the fluid is largely reduced and the fluid is monitored with precision. The actuating and sensing device may not be equipped with a power source itself. Rather, the actuating and sensing device may be coupled to an external power supply device for energy transfer, thereby enabling the sensor and the actuating device, and powering the power controller and the microprocessor for operation. Accordingly, the configuration described above saves a lot of space when installing the entire module, and the purpose of minimizing the design of the module is achieved. Moreover, the configuration described above can be applied to an electronic device for monitoring the air quality.

In accordance with an aspect of the present disclosure, a driving system for an actuating and sensing module is provided. The system includes an actuating and sensing device and a power supply device. The actuating and sensing device includes at least one sensor, at least one actuating device, a microprocessor and a power controller. The power supply device transfers an energy to the power controller, so that the power controller receives the energy and enables the sensor and the actuating device.

The above contents of the present disclosure will become more readily apparent to those ordinarily skilled in the art after reviewing the following detailed description and accompanying drawings, in which:

BRIEF DESCRIPTION OF THE DRAWINGS

FIGS. 6A to 6E schematically illustrate the actions of the fluid actuating device of the actuating and sensing device according to the embodiment of the present disclosure.

DETAILED DESCRIPTION OF THE PREFERRED EMBODIMENT

Figure 1A:
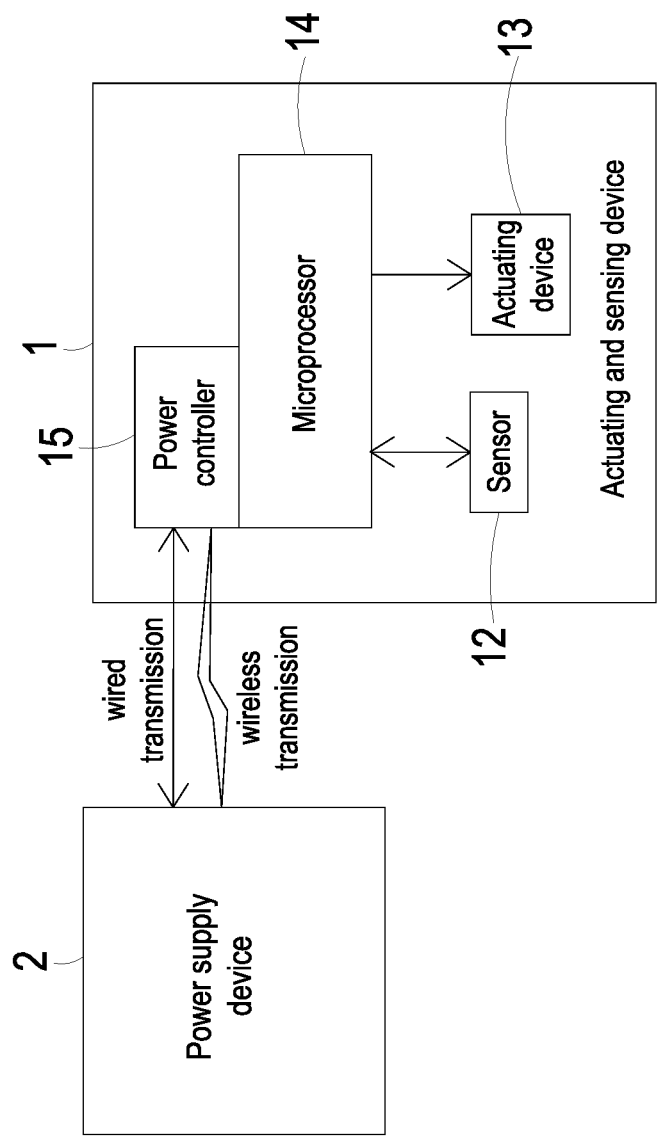
FIG. 1A schematically illustrates the architecture of a driving system for an actuating and sensing module according to a first embodiment of the present disclosure.

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Please refer to FIG. 1. The present discourse provides a driving system for an actuating and sensing module including at least one actuating and sensing device 1, at least one sensor 12, at least one actuating device 13, at least one microprocessor 14, at least one power controller 15, at least one power supply device 2 and at least one energy. The number of the actuating and sensing device 1, the microprocessor 14, the power controller 15 and the power supply device 2 is exemplified by one for each in the following embodiments but not limited thereto. It is noted that each of the actuating and sensing device 1, the microprocessor 14, the power controller 15 and the power supply device 2 can also be provided in plural numbers.

FIG. 1A schematically illustrates the architecture of a driving system for an actuating and sensing module according to a first embodiment of the present disclosure. As shown in FIG. 1A, the driving system for the actuating and sensing module includes an actuating and sensing device 1 and a power supply device 2. The actuating and sensing device 1 includes at least one sensor 12, at least one actuating device 13, a microprocessor 14 and a power controller 15. The power controller 15 receives an energy and transfers the energy to enable the sensor 12 and the actuating device 13.

An example of the sensor 12 includes but is not limited to a temperature sensor, a volatile organic compound sensor (e.g., a sensor for measuring formaldehyde or ammonia gas), a particulate sensor (e.g., a PM2.5 particle sensor), a carbon monoxide sensor, a carbon dioxide sensor, an oxygen sensor, an ozone sensor, any other appropriate gas sensor, a humidity sensor, a water content sensor, a substance sensor (e.g., a sensor for measuring compounds or biological substances in liquid or air), a water quality sensor, any other appropriate liquid sensor, a light sensor, or the combination thereof.

In an embodiment, when the actuating device 13 is enabled to drive a fluid to pass through the sensor 12, the sensor 12 is provided with the amount of fluid stably and uniformly. Since the sensor 12 is provided with the amount of fluid stably and uniformly, the response time of the sensor 12 to the fluid is largely reduced and the fluid is monitored with precision. In some embodiments, the fluid is a gas or a liquid, but not limited thereto.

The power supply device 2 transfers the energy to the power controller 15. After the power controller 15 receives the energy, the power controller 15 enables the sensor 12 and the actuating device 13. In some embodiments, the energy includes a light energy, an electric energy, a magnetic energy, a sound energy or a chemical energy, but not limited thereto.

In one embodiment, the power supply device 2 may transfer the energy through a wired transmission path. For example, the power supply device 2 is a charger or a chargeable battery, and the power supply device 2 may transfer the energy to the power controller 15 through the wired transmission path. In another embodiment, the power supply device 2 may transfer the energy to the power controller 15 through a wireless transmission path. For example, the power supply device 2 is a charger or a chargeable battery, both of which has a wireless charging component (or an induction charging component), and the power supply device 2 may transfer the energy to the power controller 15 through the wireless transmission path. In another embodiment, the power supply device 2 is a portable electronic device with wireless charging/discharging function (e.g., a smart phone). For example, the smart phone has a wireless charging component (or an induction charging component), and the smart phone may transfer the energy to the power controller 15 through the wireless transmission path.

In an embodiment, the power controller 15 further includes a chargeable element (not shown) capable of receiving and storing the energy. The chargeable element of the power controller 15 may receive and store the energy from the power supply device 2 through the wired transmission path or the wireless transmission path. Then the energy may be transferred to the sensor 12 and the actuating device 13 for powering the sensor 12 to perform a sensing operation and powering the actuating device 13 to perform an actuating operation under control.

Figure 1B:
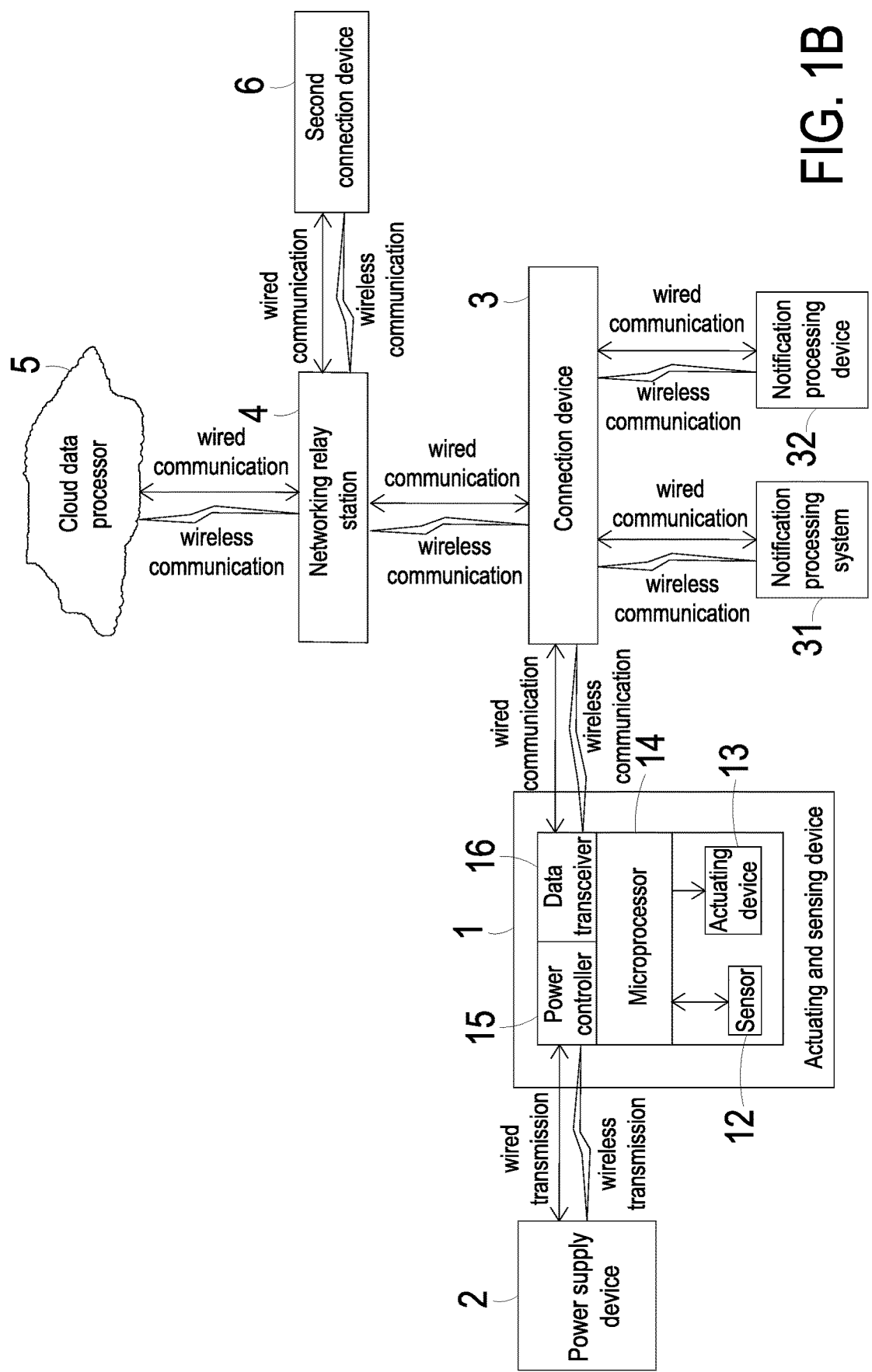
FIG. 1B schematically illustrates the architecture of a driving system for an actuating and sensing module according to a second embodiment of the present disclosure.

FIG. 1B schematically illustrates the architecture of a driving system for an actuating and sensing module according to a second embodiment of the present disclosure. As shown in FIG. 1B, the actuating and sensing device 1 of the driving system for the actuating and sensing module further includes a data transceiver 16, and the data transceiver 16 is a device for receiving or transmitting data. The driving system for the actuating and sensing module further includes a connection device 3. In this embodiment, the microprocessor 14 of the actuating and sensing device 1 is used for processing and converting the monitored data transmitted from the sensor 12 into an output data. The data transceiver 16 may receive and transmit the output data to the connection device 3. After that, the connection device 3 may display or store the information carried in the output data, or transfer the information carried in the output data to a storage device (not shown) of the connection device 3 to be stored and processed. In an embodiment, the connection device 3 is in communication with a notification processing system 31 to enable an air quality notification mechanism. For example, an instant air quality map informs people to avoid away or wear masks. In another embodiment, the connection device 3 is in communication with a notification processing device 32 to enable an air quality processing mechanism. For example, an air cleaner or an air-conditioner is enabled to clean the air.

In an embodiment, the connection device 3 is a display device with a wired communication module (e.g., a desktop computer). In another embodiment, the connection device 3 is a display device with a wireless communication module (e.g., a notebook computer). In another embodiment, the connection device 3 is a portable electronic device with a wireless communication module (e.g., a mobile phone). The wired communication module may have an RS485 communication port, an RS232 communication port, a Modbus communication port or a KNX communication port for wired communication. The wireless communication module may perform wireless communication through a Zigbee communication technology, a Z-wave communication technology, an RF communication technology, a Bluetooth communication technology, a Wifi communication technology or an EnOcean communication technology.

The driving system for the actuating and sensing module further includes a networking relay station 4 and a cloud data processor 5. The connection device 3 is used to transmit the output data to the networking relay station 4. Then the output data is transmitted from the networking relay station 4 to the cloud data processor 5 to be stored and processed. After the output data is processed by the cloud data processor 5, the cloud data processor 5 issues a notification signal to the networking relay station 4. Then, the networking relay station 4 transmits the notification signal to the connection device 3. According to the notification signal, the notification processing system 31 connected with the connection device 3 enables an air quality notification mechanism. Alternatively, the notification processing device 32 connected with the connection device 3 enables an air quality processing mechanism.

In an embodiment, the connection device 3 issues a control command to the actuating and sensing device 1 so as to control the operation of the actuating and sensing device 1. Similarly, the control command may be transmitted to the data transceiver 16 through wired communication or wireless communication. Then, the control command is transmitted to the microprocessor 14 to control the sensor 12 to perform the sensing operation and enable the actuating device 13.

In an embodiment, the driving system for the actuating and sensing module further includes a second connection device 6 for issuing a control command. After the second connection device 6 issues the control command to the cloud data processor 5 through the networking relay station 4, the control command is transmitted from the cloud data processor 5 to the connection device 3 through the networking relay station 4, so that the connection device 3 issues the control command to the data transceiver 16. Then, the control command is transmitted to the microprocessor 14. According to the control command, the microprocessor 14 controls the sensor 12 to perform the sensing operation and enables the actuating device 13. In an embodiment, the second connection device 6 is a device with a wired communication module. In other embodiment, the second connection device 6 is a device with a wireless communication module. In another embodiment, the second connection device 6 is a portable electronic device with a wireless communication module, but not limited thereto.

The actuating device 13 is a driving device capable of driving a desired system in response to a control signal. An example of the actuating device 13 includes but is not limited to an electric actuating device, a magnetic actuating device, a thermal actuating device, a piezoelectric actuating device, and a fluid actuating device. For example, the electric actuating device is an electric actuating device of a DC motor, an AC motor or a step motor, the magnetic actuating device is an magnetic actuating device of a magnetic coil motor, the thermal actuating device is a thermal actuating device of a heat pump, the piezoelectric actuating device is a piezoelectric actuating device of a piezoelectric pump, and the fluid actuating device is a fluid actuating device of a gas pump or a liquid pump.

Figure 2:
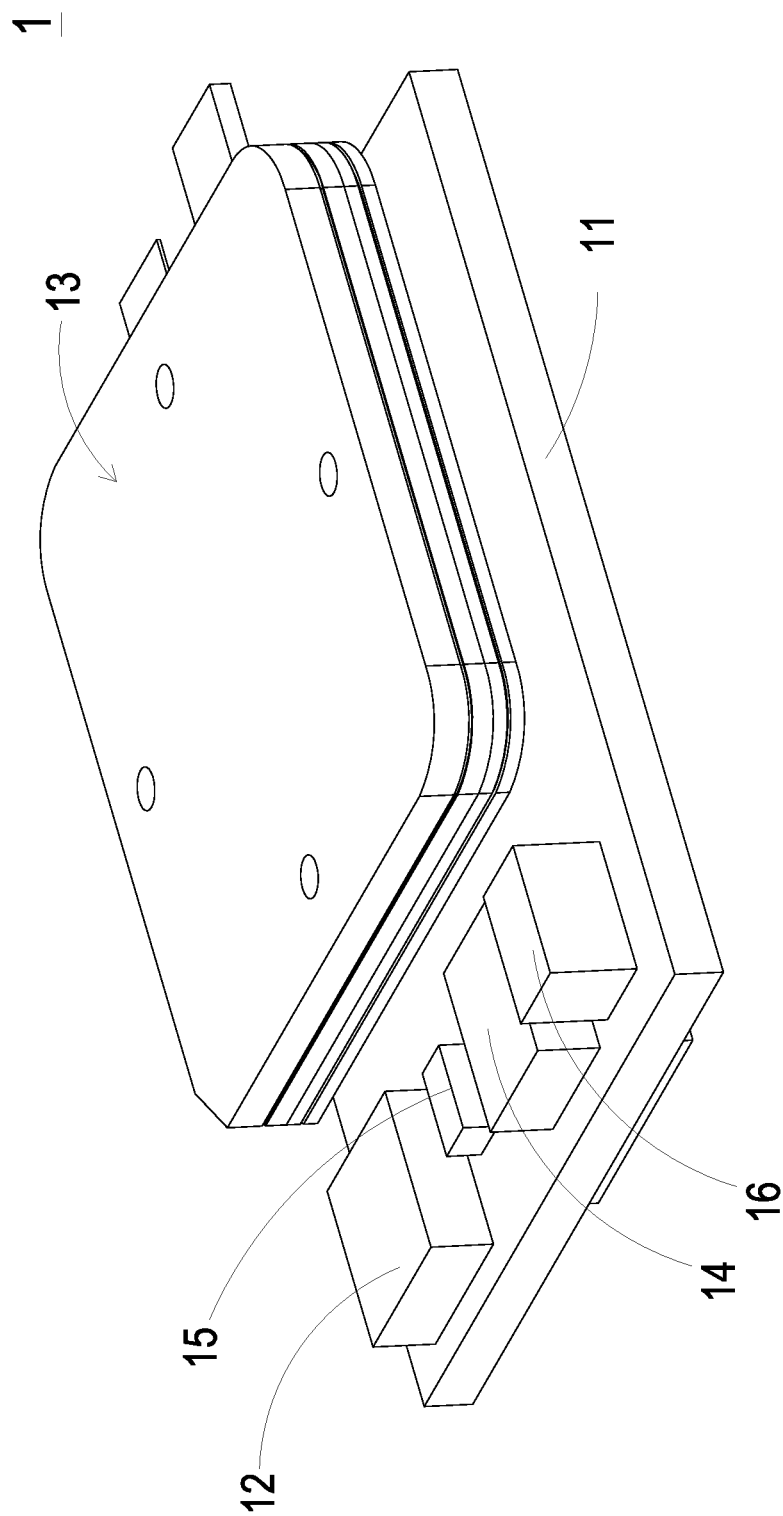
FIG. 2 is a schematic perspective view illustrating the structure of an actuating and sensing device of the driving system for the actuating and sensing module according to an embodiment of the present disclosure.

FIG. 2 is a schematic perspective view illustrating the structure of an actuating and sensing device of the driving system for the actuating and sensing module according to an embodiment of the present disclosure. The actuating and sensing device 1 further includes a carrier 11. The at least one sensor 12, the at least one actuating device 13, the microprocessor 14, the power controller 15 and the data transceiver 16 are integrated on the carrier 11 to form a modularized structure. In an embodiment, the carrier 11 is a substrate such as a printed circuit board (PCB), upon which the sensor(s) 12 and the fluid actuating device(s) 13 may be disposed in an array. In another embodiment, the carrier 11 is an application-specific integrated circuit (ASIC). In other embodiment, the carrier 11 is a system on chip (SOC). The sensor 12 is deposited on the carrier 11. The actuating device 13 is packaged on the carrier 11. That is, the carrier 11, the sensor 12 and the actuating device 13 are combined together as an integral structure. The profile and type of the carrier 11 are not restricted as long as the sensor 12 and the actuating device 13 are supported by the carrier 11.

Figure 3A:
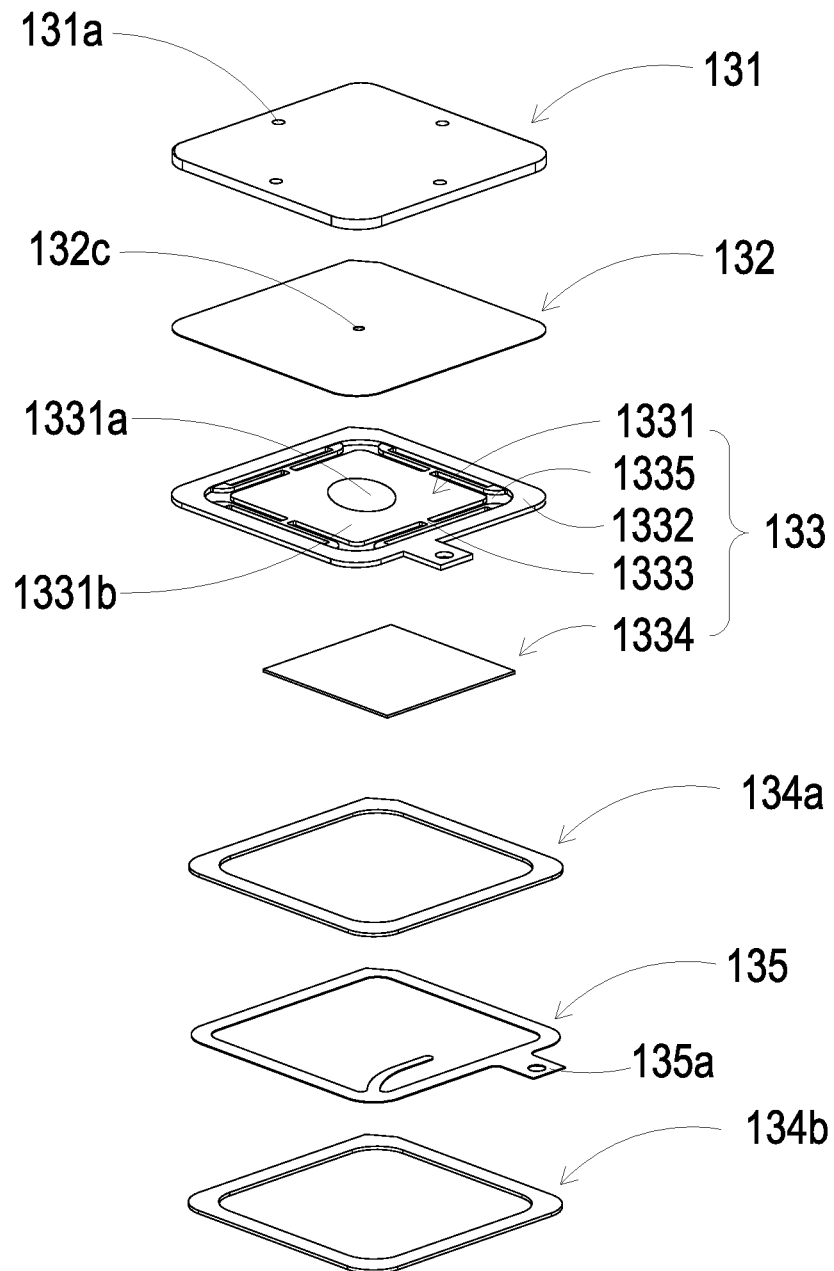
FIG. 3A is a schematic exploded view illustrating a fluid actuating device used in the actuating and sensing device of the present disclosure.
Figure 3B:
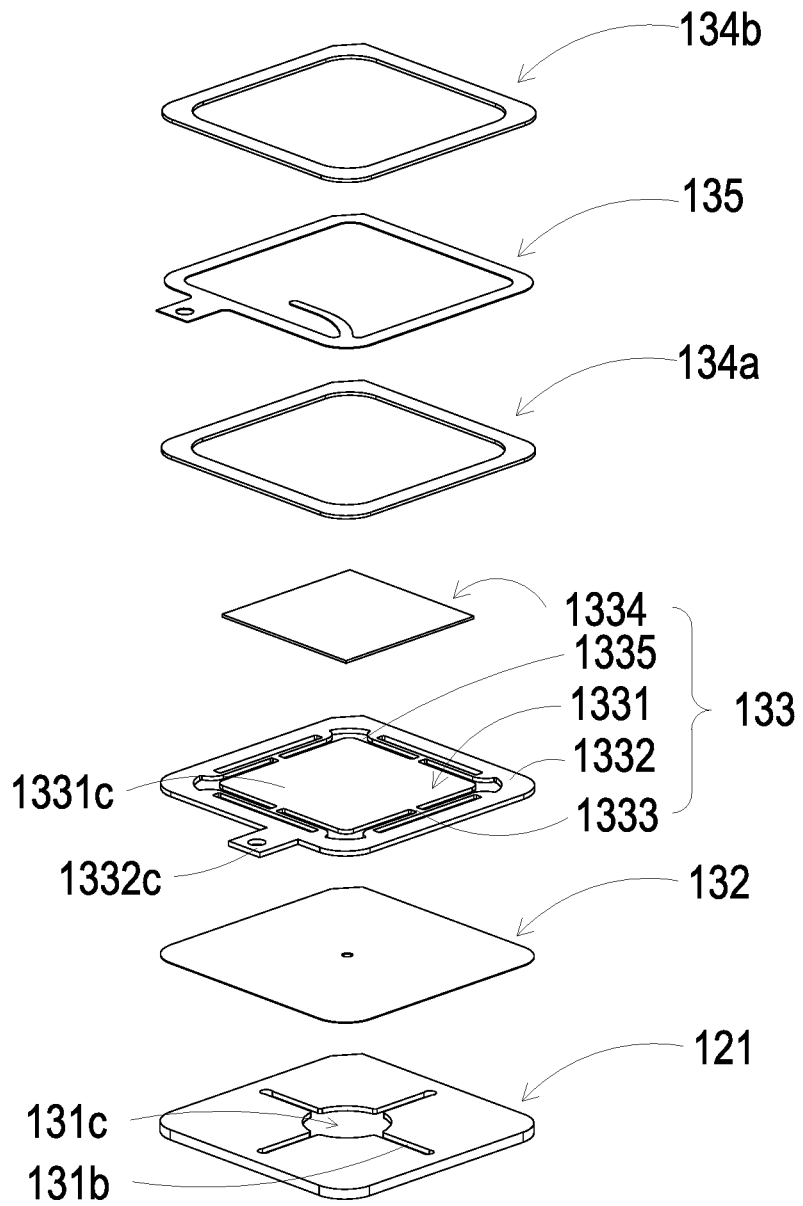
FIG. 3B is a schematic exploded view illustrating the fluid actuating device of FIG. 3A and taken along another viewpoint.

Please refer to FIG. 3A and FIG. 3B. In this embodiment, the actuating device 13 is a fluid actuating device. The fluid actuating device 13 may be a driving structure of a piezoelectric pump or a driving structure of a micro-electromechanical system (MEMS) pump. Hereinafter, the actions of the fluid actuating device 13 of a piezoelectric pump will be described as follows.

Figure 5:
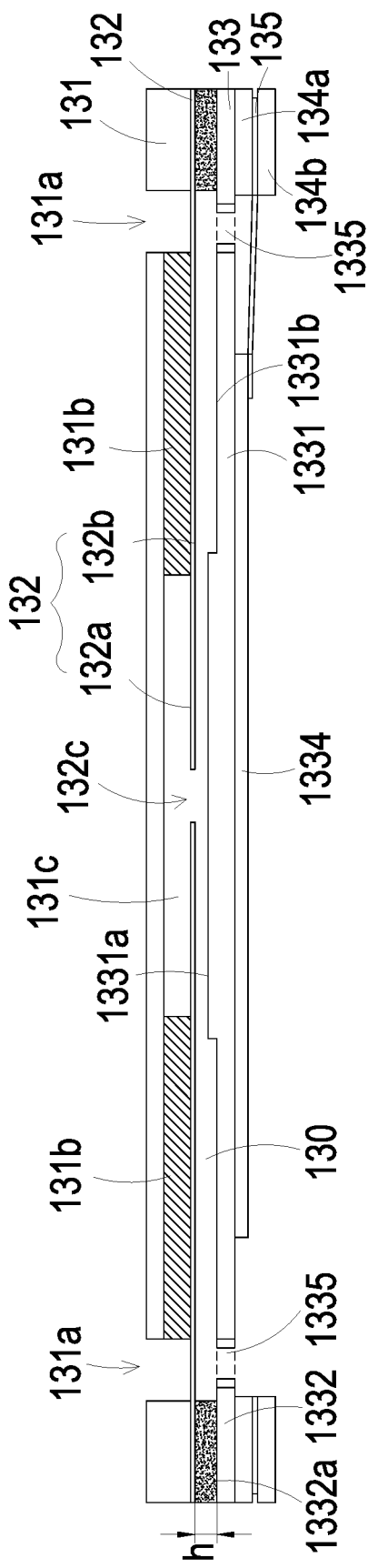
FIG. 5 is a schematic cross-sectional view illustrating the fluid actuating device as shown in FIGS. 3A and 3B.

Referring to FIGS. 3A and 3B again. The fluid actuating device 13 includes a fluid inlet plate 131, a resonance plate 132, a piezoelectric actuator 133, a first insulation plate 134a, a conducting plate 135 and a second insulation plate 134b. The piezoelectric actuator 133 is aligned with the resonance plate 132. The fluid inlet plate 131, the resonance plate 132, the piezoelectric actuator 133, the first insulation plate 134a, the conducting plate 135 and the second insulation plate 134b are stacked on each other sequentially. After the above components are combined together, the cross-sectional view of the resulting structure of the fluid actuating device 13 is shown in FIG. 5.

The fluid inlet plate 131 has at least one inlet 131a. Preferably but not exclusively, the fluid inlet plate 131 has four inlets 131a. The inlets 131a run through the fluid inlet plate 131. In response to the action of the atmospheric pressure, the fluid can be introduced into the fluid actuating device 13 through the at least one inlet 131a. Moreover, at least one convergence channel 131b is formed on a first surface of the fluid inlet plate 131, and is in communication with the at least one inlet 131a on a second surface of the fluid inlet plate 131. Moreover, a central cavity 131c is located at the intersection of the convergence channels 131b. The central cavity 131c is in communication with the at least one convergence channel 131b, such that the fluid entered by the at least one inlet 131a would be introduced into the at least one convergence channel 131b and is guided to the central cavity 131c. Consequently, the fluid can be transferred by the fluid actuating device 13. In this embodiment, the at least one inlet 131a, the at least one convergence channel 131b and the central cavity 131c of the fluid inlet plate 131 are integrally formed in one piece. The central cavity 131c is a convergence chamber for temporarily storing the fluid. In some embodiments, the fluid inlet plate 131 may be, for example, made of stainless steel. Moreover, the depth of the convergence chamber defined by the central cavity 131c is equal to the depth of the at least one convergence channel 131b. The resonance plate 132 is made of a flexible material. The resonance plate 132 has a central aperture 132c corresponding to the central cavity 131c of the fluid inlet plate 131, so as to allow the air to flow therethrough. In other embodiments, the resonance plate 132 may be, for example, made of copper.

The piezoelectric actuator 133 includes a suspension plate 1331, an outer frame 1332, at least one bracket 1333 and a piezoelectric plate 1334. The piezoelectric plate 1334 is attached on a first surface 1331c of the suspension plate 1331. In response to an applied voltage, the piezoelectric plate 1334 would be subjected to a deformation. When the piezoelectric plate 1334 is subjected to the deformation, it facilitates a bending vibration of the suspension plate 1331. In this embodiment, the at least one bracket 1333 is connected between the suspension plate 1331 and the outer frame 1332, while the two ends of the bracket 1333 are connected with the outer frame 1332 and the suspension plate 1331 respectively that the bracket 1333 can elastically support the suspension plate 1331. At least one vacant space 1335 is formed between the bracket 1333, the suspension plate 1331 and the outer frame 1332. The at least one vacant space 1335 is in communication with a fluid channel for allowing the fluid to go through. The type of the suspension plate 1331 and the outer frame 1332 and the type and the number of the at least one bracket 1333 may be varied according to the practical requirements. The outer frame 1332 is arranged around the suspension plate 1331. Moreover, a conducting pin 1332c is protruded outwardly from the outer frame 1332 so as to be electrically connected with an external circuit (not shown).

Figure 4:
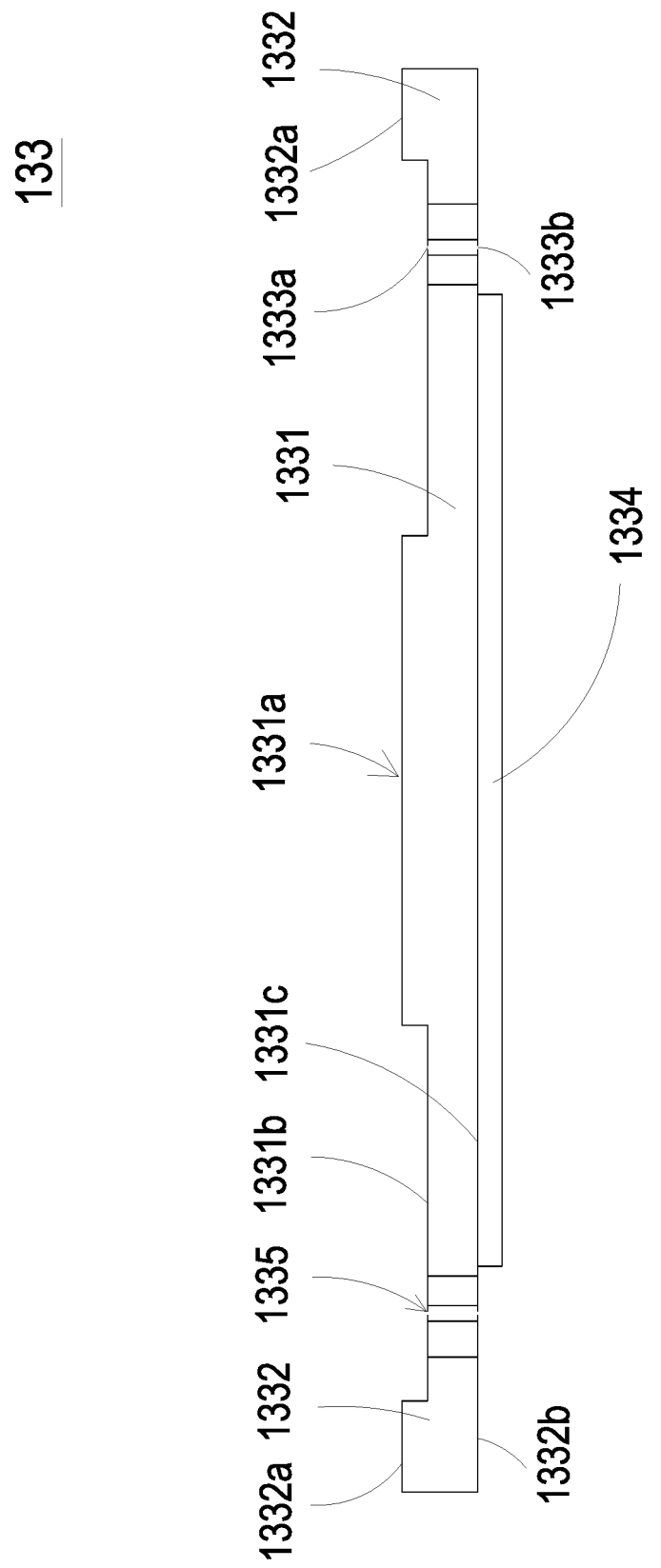
FIG. 4 is a schematic cross-sectional view illustrating the piezoelectric actuator of the fluid actuating device as shown in FIGS. 3A and 3B.

As shown in FIG. 4, the suspension plate 1331 has a bulge 1331a that makes the suspension plate 1331 a stepped structure. The bulge 1331a is formed on a second surface 1331b of the suspension plate 1331. The bulge 1331a may be a circular convex structure. A top surface of the bulge 1331a of the suspension plate 1331 is coplanar with a second surface 1332a of the outer frame 1332, while the second surface 1331b of the suspension plate 1331 is coplanar with a second surface 1333a of the bracket 1333. Moreover, there is a drop of specified amount from the bulge 1331a of the suspension plate 1331 (or the second surface 1332a of the outer frame 1332) to the second surface 1331b of the suspension plate 1331 (or the second surface 1333a of the bracket 1333). A first surface 1331c of the suspension plate 1331, a first surface 1332b of the outer frame 1332 and a first surface 1333b of the bracket 1333 are coplanar with each other. The piezoelectric plate 1334 is attached on the first surface 1331c of the suspension plate 1331. In some other embodiments, the suspension plate 1331 may be a square plate structure with two flat surfaces, but the type of the suspension plate 1331 may be varied according to the practical requirements. In this embodiment, the suspension plate 1331, the at least bracket 1333 and the outer frame 1332 may be integrally formed and produced from a metal plate (e.g., a stainless steel plate). In an embodiment, the length of a side of the piezoelectric plate 1334 is smaller than the length of a side of the suspension plate 1331. In another embodiment, the length of a side of the piezoelectric plate 1334 is equal to the length of a side of the suspension plate 1331. Similarly, the piezoelectric plate 1334 is a square plate structure corresponding to the suspension plate 1331 in terms of the design.

Please refer to FIG. 3A. In this embodiment, in the fluid actuating device 13, the first insulation plate 134a, the conducting plate 135 and the second insulation plate 134b are stacked on each other sequentially and located under the piezoelectric actuator 133. The profiles of the first insulation plate 134a, the conducting plate 135 and the second insulation plate 134b substantially match the profile of the outer frame 1332 of the piezoelectric actuator 133. In some embodiments, the first insulation plate 134a and the second insulation plate 134b are made of an insulating material (e.g. a plastic material) for providing insulating efficacy. In other embodiments, the conducting plate 135 may be made of an electrically conductive material (e.g. a metallic material) for providing electrically conducting efficacy. In this embodiment, the conducting plate 135 may have a conducting pin 135a disposed thereon so as to be electrically connected with an external circuit (not shown).

Please refer to FIG. 5. In an embodiment, the fluid inlet plate 131, the resonance plate 132, the piezoelectric actuator 133, the first insulation plate 134a, the conducting plate 135 and the second insulation plate 134b of the fluid actuating device 13 are stacked on each other sequentially. Moreover, there is a gap h between the resonance plate 132 and the outer frame 1332 of the piezoelectric actuator 133. In this embodiment, the gap h between the resonance plate 132 and the outer frame 1332 of the piezoelectric actuator 133, may be filled with a filler (e.g., a conductive adhesive) so that a depth from the resonance plate 132 to the bulge 1331a of the suspension plate 1331 of the piezoelectric actuator 133 can be maintained. The gap h ensures the proper distance between the resonance plate 132 and the bulge 1331a of the suspension plate 1331 of the piezoelectric actuator 133, so that the fluid can be transferred quickly, the contact interference is reduced and the generated noise is largely reduced. In some embodiments, alternatively, the height of the outer frame 1332 of the piezoelectric actuator 133 is increased, so that the gap is formed between the resonance plate 132 and the piezoelectric actuator 133.

Please refer to FIG. 3A, FIG. 3B and FIG. 5. After the fluid inlet plate 131, the resonance plate 132 and the piezoelectric actuator 133 are combined together, a movable part 132a and a fixed part 132b of the resonance plate 132 are defined. A convergence chamber for converging the fluid is defined by the movable part 132a of the resonance plate 132 and the fluid inlet plate 131 collaboratively. Moreover, a first chamber 130 is formed between the resonance plate 132 and the piezoelectric actuator 133 for temporarily storing the fluid. Through the central aperture 132c of the resonance plate 132, the first chamber 130 is in communication with the central cavity 131c of the fluid inlet plate 131. The peripheral regions of the first chamber 130 are in communication with the fluid channel through the vacant space 1335 between the brackets 1333 of the piezoelectric actuator 133.

Figure 6A:
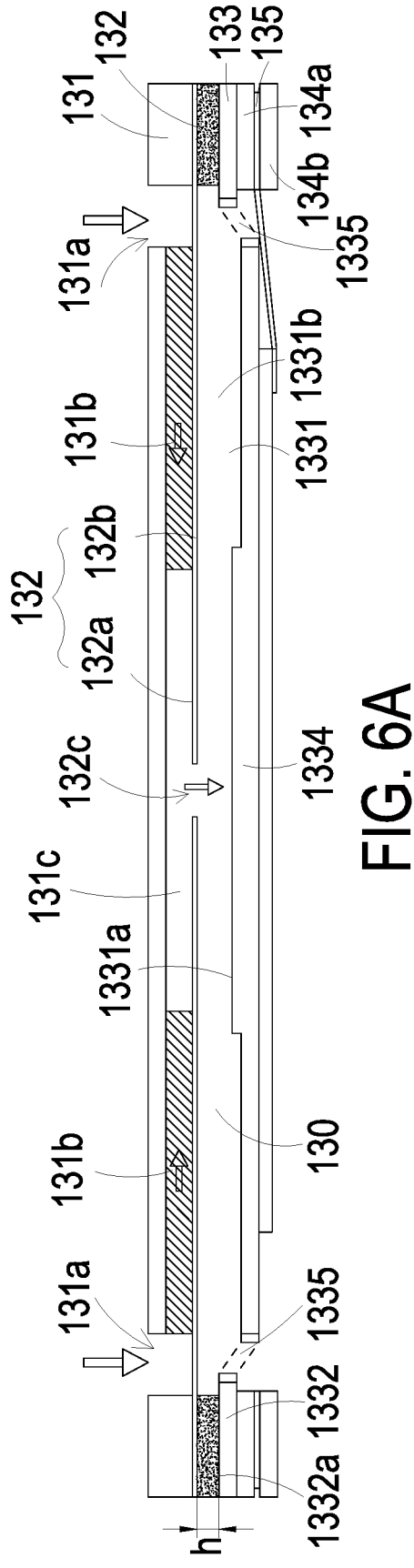
Figure 6D:
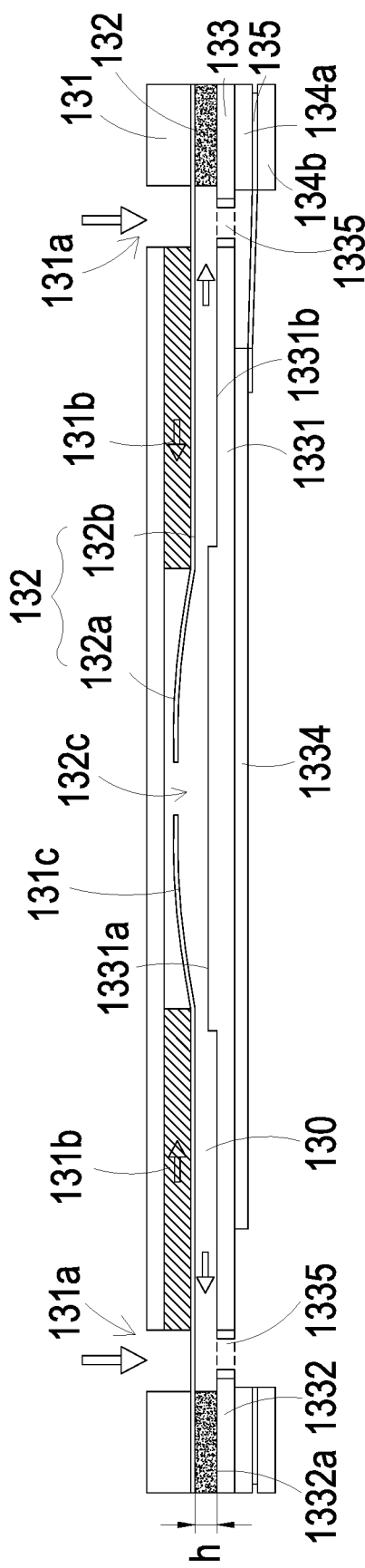
Figure 6E:
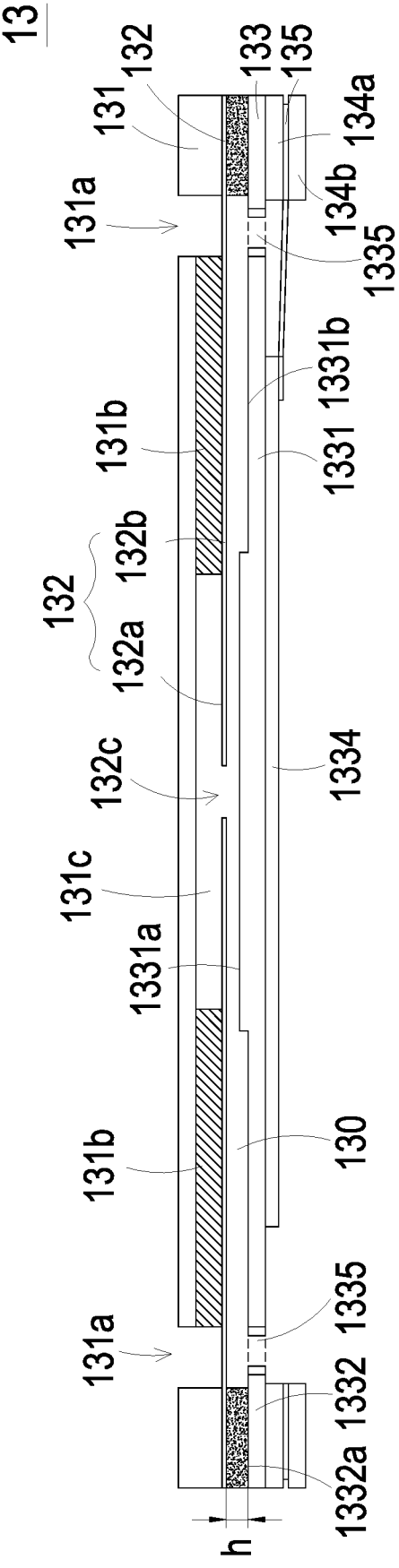

FIGS. 6A to 6E schematically illustrate the actions of the fluid actuating device of the actuating and sensing device according to the embodiment of the present disclosure. Please refer to FIG. 3A, FIG. 3B, FIG. 5 and FIGS. 6A to 6E. The actions of the fluid actuating device 13 will be described as follows. When the fluid actuating device 13 is enabled, the piezoelectric actuator 133 vibrates along a vertical direction in a reciprocating manner by using the bracket 1333 as a fulcrum. Please refer to FIG. 6A, the piezoelectric actuator 133 vibrates downwardly in response to the applied voltage. Since the resonance plate 132 is light and thin, the resonance plate 132 vibrates along the vertical direction in resonance with the piezoelectric actuator 133. More especially, a region of the resonance plate 132 spatially corresponding to the central cavity 131c of the fluid inlet plate 131 is also subjected to a bending deformation. The region of the resonance plate 132 corresponding to the central cavity 131c of the fluid inlet plate 131 is the movable part 132a of the resonance plate 132. When the piezoelectric actuator 133 vibrates downwardly, the movable part 132a of the resonance plate 132 is subjected to the bending deformation because the movable part 132a of the resonance plate 132 is pushed by the fluid and vibrates in response to the piezoelectric actuator 133. In response to the downward vibration of the piezoelectric actuator 133, the fluid is fed into the at least one inlet 131a of the fluid inlet plate 131. Then, the fluid is transferred to the central cavity 131c of the fluid inlet plate 131 through the at least one convergence channel 131b. Then, the fluid is transferred through the central aperture 132c of the resonance plate 132 spatially corresponding to the central cavity 131c, and introduced downwardly into the first chamber 130. As the piezoelectric actuator 133 is enabled, the resonance of the resonance plate 132 occurs. Consequently, the resonance plate 132 vibrates along the vertical direction in the reciprocating manner. As shown in FIG. 6B, during the vibration of the movable part 132a of the resonance plate 132 at this stage, the movable part 132a of the resonance plate 132 moves down to contact and attach on the bulge 1331a of the suspension plate 1331 of the piezoelectric actuator 133, and a distance from the fixed part 132b of the resonance plate 132 to a region of the suspension plate 1331 except the bulge 1331a remains the same. Owing to the deformation of the resonance plate 132 described above, a middle communication space of the first chamber 130 is closed, and the volume of the first chamber 130 is compressed. Under this circumstance, the pressure gradient occurs to push the fluid in the first chamber 130 moving toward peripheral regions of the first chamber 130 and flowing downwardly through the vacant space 1335 of the piezoelectric actuator 133. Referring to FIG. 6C, the movable part 132a of the resonance plate 132 has returned to its original position when the piezoelectric actuator 133 vibrates upwardly. Consequently, the volume of the first chamber 130 is continuously compressed to generate the pressure gradient which makes the fluid in the first chamber 130 continuously pushed toward peripheral regions. Meanwhile, the fluid is continuously fed into the at least one inlet 131a of the fluid inlet plate 131, and transferred to the central cavity 131c. Then, as shown in FIG. 6D, the resonance plate 132 moves upwardly, which is cause by the resonance of the upward motion of the piezoelectric actuator 133. That is, the movable part 132a of the resonance plate 132 is also vibrated upwardly. Consequently, it decreases the current of the fluid from the at least one inlet 131a of the fluid inlet plate 131 into the central cavity 131c. At last, as shown in FIG. 6E, the movable part 132a of the resonance plate 132 has returned to its original position. As the embodiments described above, when the resonance plate 132 vibrates along the vertical direction in the reciprocating manner, the gap h between the resonance plate 132 and the piezoelectric actuator 133 is helpful to increase the maximum displacement along the vertical direction during the vibration. In other words, the configuration of the gap h between the resonance plate 132 and the piezoelectric actuator 133 can increase the amplitude of vibration of the resonance plate 132. Consequently, a pressure gradient is generated in the fluid guiding channels of the fluid actuating device 13 to facilitate the fluid to flow at a high speed. Moreover, since there is an impedance difference between the feeding direction and the exiting direction, the fluid can be transmitted from the inlet side to the outlet side. Even if a gas pressure (which may impede the fluid flow) exists at the outlet side, the fluid actuating device 13 still has the capability of pushing the fluid to the fluid channel while achieving the silent efficacy. The steps of FIGS. 6A to 6E may be done repeatedly. Consequently, the ambient fluid is transferred by the fluid actuating device 13 from the outside to the inside.

After the fluid inlet plate 131, the resonance plate 132, the piezoelectric actuator 133, the first insulation plate 134a, the conducting plate 135 and the second insulation plate 134b are stacked on each other sequentially, the fluid actuating device 13 is assembled. After the fluid actuating device 13 is installed on the carrier 11, the at least one fluid channel (not shown) is arranged between the fluid actuating device 13 and the carrier 11. The fluid channel is arranged beside one lateral side of the sensor 12. When the fluid actuating device 13 is enabled to compress the fluid, the fluid is transferred through the fluid channel and the fluid is sensed by the sensor 12. Accordingly, the configuration inside the fluid actuating device 13 may help guide the fluid flow in a desired direction and provide the amount of fluid stably and uniformly to the sensor 12. Since the sensor 12 is provided with the amount of the fluid stably and uniformly, the response time of the sensor to the fluid is largely reduced and the fluid is monitored with precision. Moreover, the actuating and sensing device 1 may not be equipped with a power source itself. Rather, the actuating and sensing device 1 may be coupled to an external power supply device 2 for energy transfer, thereby enabling the sensor 12 and the actuating device 13, and powering the power controller 15, the data transceiver 16 and the microprocessor 14 for operation. Accordingly, the configuration described above saves a lot of space when installing the entire module, and the purpose of minimizing the design of the module is achieved. Moreover, the configuration described above can be applied to an electronic device for monitoring the air quality. Moreover, the data transceiver 16 receives a control command to control the sensor 12 to perform sensing operation and enable the actuating device 13. After the monitored data sensed by the at least one sensor 12 is transmitted to the microprocessor 14, the monitored data is processed into an output data. The output data is transmitted to the connection device 3. The output data is displayed, stored and transmitted by the connection device 3. Consequently, the purpose of immediately displaying the output data and issuing the notification signal are achieved. Moreover, the output data can be transmitted to a cloud database. Consequently, the purpose of constructing and managing the data can be achieved. Accordingly, an air quality notification mechanism and an air quality processing mechanism are enabled.

From the above descriptions, the present disclosure provides a driving system for the actuating and sensing module. The system includes an actuating and a power supply device. The actuating and sensing device includes at least one sensor, at least one actuating device, a microprocessor, and a power controller. The at least one sensor, the at least one actuating device, the microprocessor and the power controller are integrated as a modularized structure. The actuating device is used to increase the flow rate of fluid and provide the amount of fluid stably and uniformly. Since the sensor is provided with the amount of the fluid stably and uniformly, the response time of the sensor to the fluid is largely reduced and the fluid is monitored with precision. The actuating and sensing device may not be equipped with a power source itself. Rather, the actuating and sensing device may be coupled to an external power supply device for energy transfer, thereby enabling the sensor and the actuating device, and powering the power controller and the microprocessor for operation. Accordingly, the configuration described above saves a lot of space when installing the entire module, and the purpose of minimizing the design of the module is achieved. Moreover, the configuration described above can be applied to an electronic device for monitoring the air quality.

Moreover, a data transceiver receives a control command to control the sensor and the actuating device. After a monitored data sensed by the at least one sensor is transmitted to the microprocessor, the monitored data is processed into an output data. The output data is transmitted to the connection device. The output data is displayed, stored and transmitted by the connection device. Consequently, the purpose of immediately displaying the output data and issuing the notification signal are achieved. Moreover, the output data can be transmitted to a cloud database. Consequently, the purpose of constructing and managing the data can be achieved. Accordingly, an air quality notification mechanism and an air quality processing mechanism are enabled. In other words, the driving system for the actuating and sensing module of the present disclosure is industrially valuable.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A driving system for an actuating and sensing module, comprising:
    an actuating and sensing device, wherein the actuating and sensing device is a modularized structure composed of at least one sensor, at least one actuating device, a microprocessor and a power controller, the actuating and sensing device further comprises a carrier, the at least one actuating device is disposed adjacent to the at least one sensor, and the at least one actuating device and the at least one sensor are disposed on a same surface of the carrier;
    a power supply device configured to transfer an energy to the power controller, so that the power controller receives the energy and enables the sensor and the actuating device.

2. The driving system for the actuating and sensing module according to claim 1, wherein the power supply device is a charger.

3. The driving system for the actuating and sensing module according to claim 2, wherein the charger transfers the energy through a wired transmission path or a wireless transmission path.

4. The driving system for the actuating and sensing module according to claim 1, wherein the power supply device is a portable electronic device with wireless charging/discharging function, and the portable electronic device transfers the energy through a wireless transmission path.

5. The driving system for the actuating and sensing module according to claim 1, wherein the power supply device is a chargeable battery.

6. The driving system for the actuating and sensing module according to claim 5, wherein the chargeable battery transfers the energy through a wired transmission path or a wireless transmission path.

7. The driving system for the actuating and sensing module according to claim 1, wherein the actuating and sensing device further comprises a chargeable element.

8. The driving system for the actuating and sensing module according to claim 7, wherein the chargeable element receives the energy from the power supply device through a wired transmission path and stores the energy, wherein the energy is transferred from the chargeable element to the sensor and the actuating device for powering the sensor to perform a sensing operation and powering the actuating device to perform an actuating operation under control.

9. The driving system for the actuating and sensing module according to claim 7, wherein the chargeable element receives the energy from the power supply device through a wireless transmission path and stores the energy, wherein the energy is transferred from the chargeable element to the sensor and the actuating device for powering the sensor to perform a sensing operation and powering the actuating device to perform an actuating operation under control.

10. The driving system for the actuating and sensing module according to claim 1, wherein the actuating and sensing device further comprises a data transceiver.

11. The driving system for the actuating and sensing module according to claim 10, wherein the actuating and sensing device further comprises a carrier, wherein the at least one sensor, the at least one actuating device, the microprocessor, the power controller and the data transceiver are integrated on the carrier to form a modularized structure.

12. The driving system for the actuating and sensing module according to claim 11, further comprising a connection device, wherein after a monitored data from the at least one sensor is processed into an output data by the microprocessor, the data transceiver receives and transmits the output data to the connection device, so as to display, store and transmit the information carried in the output data, and wherein after a control command is given by the connection device, the data transceiver receives and transmits the control command to the microprocessor to control the at least one sensor to perform a sensing operation and enable the at least one actuating device.

13. The driving system for the actuating and sensing module according to claim 11, wherein the carrier is a substrate, and the sensor and the actuating device are installed on the substrate.

14. The driving system for the actuating and sensing module according to claim 11, wherein the carrier is an application-specific integrated circuit or a system on chip, and the sensor and the actuating device are packaged thereon.

15. The driving system for the actuating and sensing module according to claim 1, wherein the actuating device comprises at least one selected from the group consisting of an electric actuating device, a magnetic actuating device, a thermal actuating device, a piezoelectric actuating device and a fluid actuating device.

16. The driving system for the actuating and sensing module according to claim 1, wherein the sensor comprises at least one selected from the group consisting of a gas sensor, an oxygen sensor, a carbon monoxide sensor, a carbon dioxide sensor, a temperature sensor, a liquid sensor, a humidity sensor, an ozone sensor, a particulate sensor, a volatile organic compound sensor and a light sensor.

17. The driving system for the actuating and sensing module according to claim 1, wherein the actuating device is a MEMS pump.

18. The driving system for the actuating and sensing module according to claim 1, wherein the actuating device is a piezoelectric pump.

19. The driving system for the actuating and sensing module according to claim 18, wherein the piezoelectric pump comprises:
    a fluid inlet plate having at least one inlet, at least one convergence channel and a central cavity defining a convergence chamber, wherein the at least one inlet allows the fluid to flow in, and wherein the convergence channel is disposed corresponds to the inlet and guides the fluid from the inlet toward the convergence chamber defined by the central cavity;
    a resonance plate having a central aperture and a movable part, wherein the central aperture is aligned with the convergence chamber and the movable part surrounds the central aperture; and a piezoelectric actuator aligned with the resonance plate, wherein a gap is formed between the resonance plate and the piezoelectric actuator to define a first chamber, so that the fluid from the at least one inlet of the fluid inlet plate is converged to the central cavity along the at least one convergence channel and flows into the first chamber through the central aperture of the resonance plate when the piezoelectric actuator is enabled, whereby the fluid is further transferred through a resonance between the piezoelectric actuator and the movable part of the resonance plate.

20. The driving system for the actuating and sensing module according to claim 19, wherein the piezoelectric actuator comprises:
a suspension plate being a square suspension plate and having a first surface, an opposing second surface and a bulge, wherein the suspension plate is permitted to undergo a bending vibration;
an outer frame arranged around the suspension plate;
at least one bracket connected between the suspension plate and the outer frame for elastically supporting the suspension plate; and
a piezoelectric plate, wherein a length of a side of the piezoelectric plate is smaller than or equal to a length of a side of the suspension plate, and the piezoelectric plate is attached on the first surface of the suspension plate, wherein when a voltage is applied to the piezoelectric plate, the suspension plate is driven to undergo the bending vibration.

21. A driving system for an actuating and sensing module, comprising:
at least one actuating and sensing device, wherein the at least one actuating and sensing device is at least one modularized structure composed of at least one sensor, at least one actuating device, at least one microprocessor and at least one power controller, the at least one actuating and sensing device further comprises at least one carrier, the at least one actuating device is disposed adjacent to the at least one sensor, and the at least one actuating device and the at least one sensor are disposed on a same surface of the at least one carrier;
at least one power supply device configured to transfer at least one energy to the power controller, so that the power controller receives the energy and enables the sensor and the actuating device.

* * * * *